United States Patent
Leone

(10) Patent No.: US 10,906,728 B2
(45) Date of Patent: Feb. 2, 2021

(54) DEVICE FOR DISPENSING A FLUID PRODUCT

(71) Applicant: APTAR FRANCE SAS, Le Neubourg (FR)

(72) Inventor: Patrice Leone, Acquigny (FR)

(73) Assignee: APTAR FRANCE SAS, Le Neubourg (FR)

( * ) Notice: Subject to any disclaimer, the term of this patent is extended or adjusted under 35 U.S.C. 154(b) by 0 days.

(21) Appl. No.: 16/621,864

(22) PCT Filed: Jun. 20, 2017

(86) PCT No.: PCT/FR2017/051626
§ 371 (c)(1),
(2) Date: Dec. 12, 2019

(87) PCT Pub. No.: WO2018/234640
PCT Pub. Date: Dec. 27, 2018

(65) Prior Publication Data
US 2020/0102141 A1    Apr. 2, 2020

(51) Int. Cl.
*B65D 83/54* (2006.01)
*A61M 15/00* (2006.01)

(52) U.S. Cl.
CPC ........... *B65D 83/54* (2013.01); *A61M 15/009* (2013.01); *A61M 15/0021* (2014.02); *A61M 15/0066* (2014.02)

(58) Field of Classification Search
CPC . B65D 83/54; A61M 15/009; A61M 15/0021; A61M 15/0066

(Continued)

(56) References Cited

U.S. PATENT DOCUMENTS

| 4,035,445 A | * | 7/1977 | Baumgartner | .......... C07C 7/163 525/54 |
| 5,474,758 A | * | 12/1995 | Kwon | .................... B65D 83/48 222/394 |

(Continued)

FOREIGN PATENT DOCUMENTS

| EP | 0 534 308 A1 | 3/1993 |
| EP | 1 200 321 A1 | 5/2002 |

(Continued)

OTHER PUBLICATIONS

International Preliminary Report on Patentability dated Dec. 24, 2019 from the International Bureau in Application No. PCT/FR2017/051626.

(Continued)

*Primary Examiner* — Paul R Durand
*Assistant Examiner* — Andrew P Bainbridge
(74) *Attorney, Agent, or Firm* — Sughrue Mion, PLLC

(57) ABSTRACT

A fluid dispenser device comprising: a body (100) that is provided with a dispenser orifice (110); a reservoir (1) containing fluid and a propellant gas; and a metering valve (20) that is assembled on said reservoir (1); said reservoir (11) being movable in said body (100) so as to actuate the metering valve (20) and dispense a dose of fluid through said dispenser orifice (110), said metering valve (20) including a valve member (30) that slides in said metering valve (20) during actuation; said device further comprising at least one sealing element (40, 41, 42) so as to form a leaktight seal, at least one sealing element (40, 41, 42) of said device comprising Cyclic Block Copolymer (CBC).

9 Claims, 3 Drawing Sheets

(58) Field of Classification Search
USPC .................................................. 222/402.24
See application file for complete search history.

(56) References Cited

U.S. PATENT DOCUMENTS

| | | | | |
|---|---|---|---|---|
| 7,824,770 | B2* | 11/2010 | Honma | B29B 15/125 |
| | | | | 428/373 |
| 9,573,749 | B2* | 2/2017 | Jacuk | B65D 83/38 |
| 10,231,948 | B2* | 3/2019 | Nguyen | A61M 15/009 |
| 2008/0017191 | A1* | 1/2008 | Davies | A61K 31/352 |
| | | | | 128/200.23 |
| 2008/0230567 | A1 | 9/2008 | Ohbi | |
| 2016/0310236 | A1* | 10/2016 | Kopelman | G06F 30/00 |
| 2020/0102141 | A1* | 4/2020 | Leone | A61M 15/009 |

FOREIGN PATENT DOCUMENTS

| | | |
|---|---|---|
| WO | 99/19235 A1 | 4/1999 |
| WO | 2010/096106 A1 | 8/2010 |

OTHER PUBLICATIONS

International Search Report for PCT/FR2017/051626 dated Mar. 23, 2018 [PCT/ISA/210].

\* cited by examiner

Styrene-Butadiene-Styrene

PCHE-EB-PCHE

DEVICE FOR DISPENSING A FLUID PRODUCT

CROSS REFERENCE TO RELATED APPLICATIONS

This application is a National Stage of International Application No. PCT/FR2017/051626 filed Jun. 20, 2017.

The present invention relates to a fluid dispenser device.

More particularly, the present invention relates to a pharmaceutical-fluid dispenser device of the metered dose inhaler type, commonly known as a pressurized Metered Dose Inhaler (pMDI). In that type of device, the pharmaceutical fluid that contains one or more active substances is associated with a propellant gas and is disposed in a reservoir under pressure. In general, the reservoir contains the fluid and the propellant gas, in particular a formulation made up of one or more active principles in suspension and/or in solution in a liquefied propellant gas, and possibly excipients. A metering valve is assembled on the reservoir and is actuated so as to dispense a dose of fluid on each actuation. Inhalers of that type comprise an outer body in which the reservoir may slide, generally axially, so as to actuate the valve and dispense the dose of fluid through a dispenser orifice, generally a mouthpiece. That type of device is well known in the state of the art. Numerous types of metering valves exist that may be used with that type of inhaler. In general, a metering valve comprises a valve body in which a valve member slides. The valve body contains a metering chamber, and when the valve member is pushed in, the metering chamber empties through said valve member under the effect of the propellant gas. When the valve member then returns to its rest position, a new dose is loaded into the metering chamber. In known manner, that type of pMDI includes one or more sealing elements. The sealing elements provide sealing at different locations, and, in conventional manner, there generally exists a neck gasket that is interposed between the metering valve, the reservoir, and the fastener ring that serves to fasten the valve on the reservoir. In addition, the valve itself includes one or more sealing gaskets that co-operate with the valve member when said valve member is at rest and/or when it moves towards its actuated position. In more common valves, the valve generally includes two gaskets known as "internal gaskets" against which the valve member slides in leaktight manner during actuation. The various sealing elements are thus likely to be in contact with the active substance contained in the fluid to be dispensed. They are also in contact with the propellant gas. Generally, the sealing elements are made out of elastomer material of the ethylene-propylene terpolymer rubber (EPDM), nitrile rubber, or polychloroprene rubber, etc. type. All of those materials perform well to a greater or lesser extent depending on the properties under consideration, and they all present certain drawbacks. In particular, they are likely to interact with the active substance and/or with the propellant gas. It is thus desirable to find materials for making such sealing elements that interact as little as possible with said active substance and/or with said propellant gas, while being easy to manufacture and to assemble, so as to be suitable for typical high-speed assembly lines for such inhalers.

Document WO 2010/096106 describes a material known as Cyclic Block Copolymer (CBC) having applications that are mainly optical, in particular the manufacture of parts for LCD screens. Other known applications of CBC include applications in the food and medical fields, in particular making parts for syringes or transparent pouches for containing fluids. However, that CBC material has never been used as a sealing element in devices of the pMDI type, and in particular in contact with propellant gases that act very aggressively on the component materials of sealing elements. However, it has been observed, surprisingly, that CBC material turns out to be particularly beneficial and suitable for being used in metering valve applications in which said valve functions with propellant gases, in particular of the hydrofluoroalkane (HFA) type.

An object of the present invention is thus to provide a fluid dispenser device that does not have the above-mentioned drawbacks.

More particularly, an object of the present invention is to provide a fluid dispenser device that improves the properties of the sealing elements used in the device, and that limits the damaging interactions between said sealing elements and the fluid and/or the propellant gas with which it is in contact.

Another object of the present invention is to provide a fluid dispenser device that is simple and inexpensive to manufacture and to assemble.

The present invention thus provides a fluid dispenser device comprising: a body that is provided with a dispenser orifice; a reservoir containing fluid and a propellant gas; and a metering valve that is assembled on said reservoir; said reservoir being movable in said body so as to actuate the metering valve and dispense a dose of fluid through said dispenser orifice, said metering valve including a valve member that slides in said metering valve during actuation; said device further comprising at least one sealing element so as to form a leaktight seal, at least one sealing element of said device comprising Cyclic Block Copolymer (CBC).

Advantageously, said metering valve is assembled on said reservoir with a neck gasket interposed therebetween.

Advantageously, said metering valve includes at least one internal gasket that co-operates in leaktight manner with said valve member.

Advantageously, said metering valve includes an upper internal gasket and a lower internal gasket, defining between them a metering chamber of said metering valve.

Advantageously, said neck gasket and/or said upper internal gasket and/or said lower internal gasket comprise(s) CBC.

Advantageously, said at least one sealing element is constituted by CBC.

Advantageously, said fluid is a pharmaceutical fluid containing at least one active substance.

Advantageously, said propellant gas comprises HFA gases, in particular of the HFA 134a and/or HFA 227 and/or HFA 152a type.

Advantageously, a ring is associated with the metering valve, at least one sealing element made of CBC being over-molded on a portion of said metering valve and/or of said ring.

These advantages and others of the present invention appear more clearly from the following detailed description, given by way of non-limiting examples, and with reference to the accompanying drawings, and in which.

Figure 1:
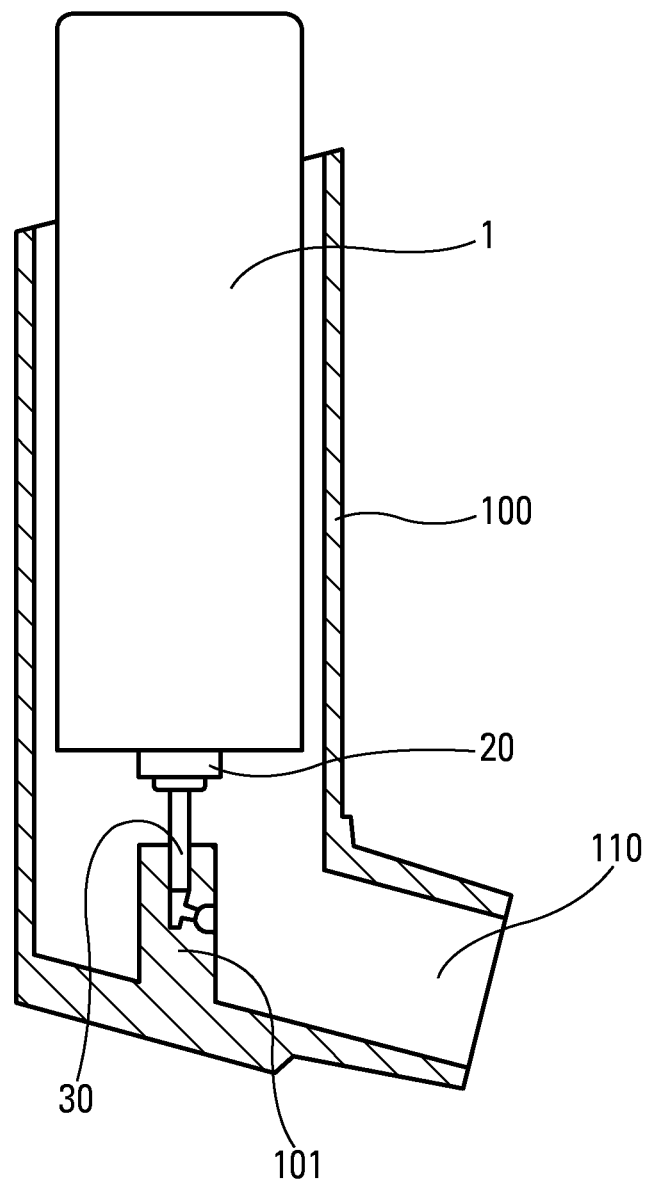
FIG. 1 is a diagrammatic section view of a fluid dispenser device of the pressurized Metered Dose Inhaler (pMDI) type.

With reference to FIG. 1, there is described a metered dose inhaler, generally known as a pMDI, that conventionally includes an outer body 100 provided with a dispenser orifice 110, generally a mouthpiece. Inside the body there is disposed a reservoir 1 on which a metering valve 20 is mounted. A valve member 30 slides in said metering valve 20 so as to dispense a dose of fluid on each actuation. The body 100 includes a well 101 that receives the valve member 30, and that creates a connection passage between the outlet of the valve member 30 and said dispenser orifice 110. In conventional manner, in order to actuate such a device, the user presses on the end of the reservoir 1 so as to push said reservoir axially inside the body 100, thereby causing the valve member 30 to slide in leaktight manner into the metering valve 20, thereby causing a dose of fluid to be dispensed. Inside the reservoir, the fluid, which generally contains one or more active substances, is associated with a propellant gas, preferably a gas of the HFA type, e.g. HFA 134a (1,1,1,2-tetrafluoroethane) and/or HFA 227 (1,1,1,2,3,3,3-heptafluoropropane) and/or HFA 152a (1,1-difluoroethane).

Figure 2:
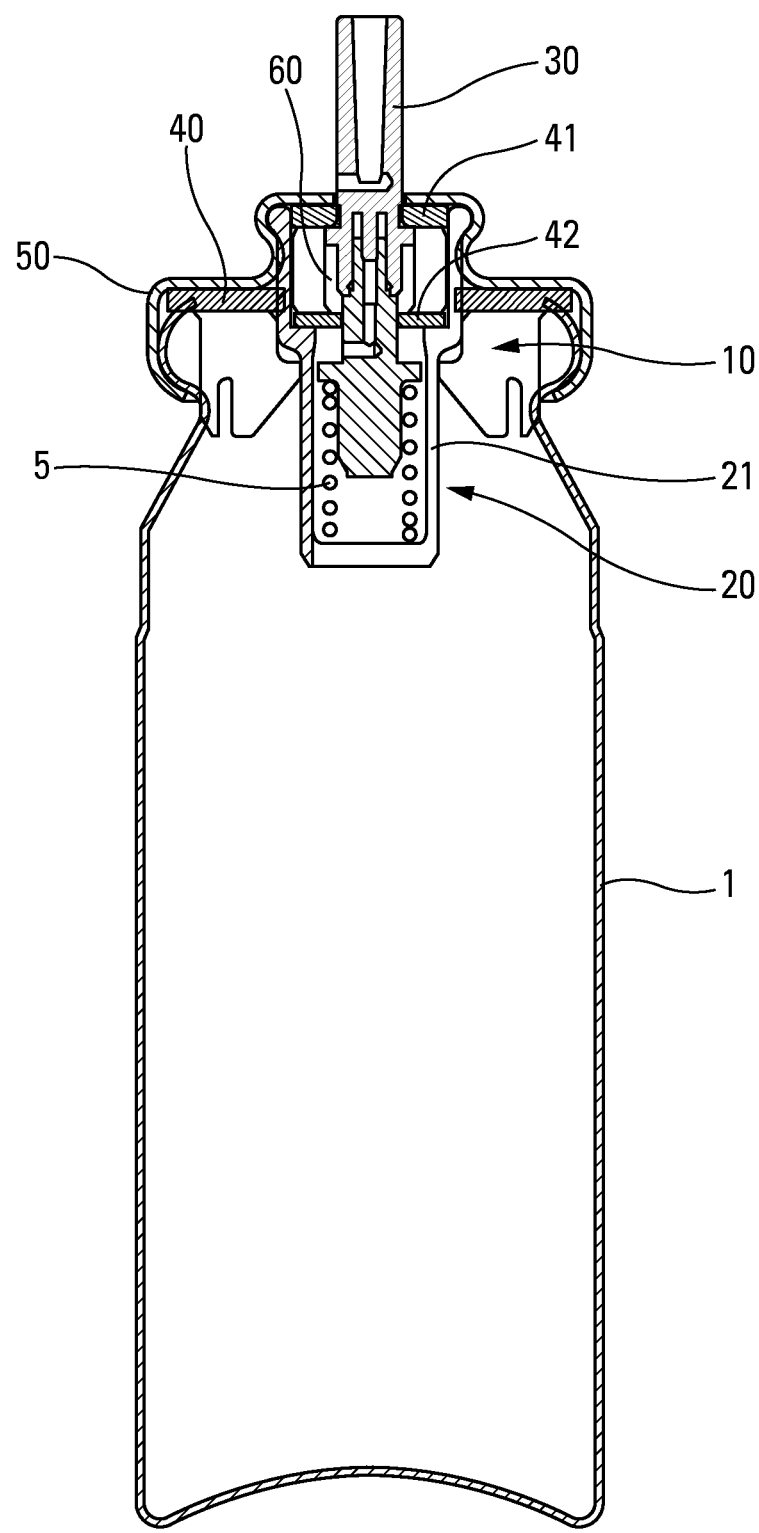
FIG. 2 is a diagrammatic section view of a reservoir on which a metering valve is assembled, in an advantageous embodiment of the present invention.

FIG. 2 shows a metering valve in a particular advantageous embodiment. Naturally, the present invention is not limited to that type of metering valve, but applies to any type of metering valve that can be used in pMDIs.

A metering valve 20 is assembled on the reservoir 1, as can be seen in FIG. 2. Assembly may be achieved by means of a fastener ring 50 that, in this configuration, is a ring fastened by crimping, but that could also be a ring that is snap-fastened or screw-fastened. The metering valve 20 conventionally comprises a metering valve 21 inside which a valve member 30 slides. The valve member 30 is urged by a spring 5 towards its rest position.

In known manner, a sealing gasket 40 known as a "neck gasket" is interposed between the fastener ring 50 and the neck of the reservoir 1 while the metering valve 20 is being assembled on the reservoir 1, so as to provided sealing at the neck of the reservoir.

In addition, the metering valve includes at least one internal sealing gasket 41, 42 that co-operates in leaktight manner with the valve member 30. In the embodiment shown in FIG. 2, the valve includes an upper internal gasket 41 and a lower internal gasket 42, the terms "lower" and "upper" referring to the orientation in FIG. 2, i.e. with the valve 20 disposed above the reservoir 1. A metering chamber 60 is defined between the two internal gaskets 41, 42, and when the valve member 30 is pushed into the valve body 21, the contents of the metering chamber 60 are expelled through the valve member 30 in conventional manner.

A ring 10 may be interposed between the neck gasket 40 and the valve body 21 so as to limit contact between the active substance and the neck gasket 40, but also so as to limit the dead volume in this location of the device. When present, the ring 10 may be of any appropriate shape and material.

In the invention, at least one of the sealing elements, i.e. at least one of the neck gasket 40, the upper internal gasket 41, and the lower internal gasket 42, comprise Cyclic Block Copolymer (CBC).

Preferably, the three above-mentioned gaskets are made of that material.

Advantageously, CBC forms the only base material, but it is possible to envisage making a CBC alloy with one or more other materials, in particular of the elastomer type.

CBC is manufactured and sold in particular by the supplier USI CORPORATION, in particular under the trade name Puratran™.

Figure 3:
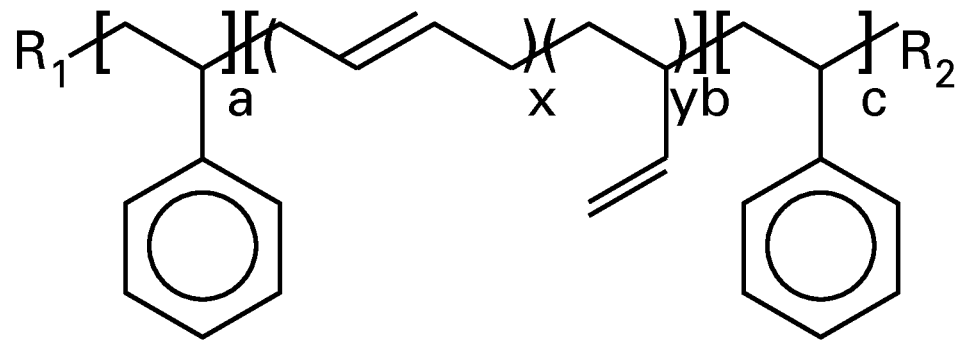
FIG. 3 shows the chemical structure of CBC and its method of manufacture by hydrogenating styrene-butadiene-styrene (SBS).
Figure 3:
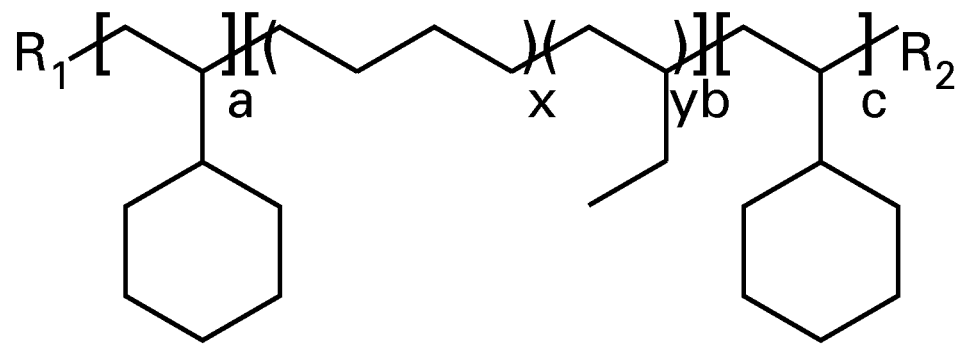

CBC is a material obtained by hydrogenating styrene-butadiene-styrene (SBS) completely, as shown in FIG. 3.

Thus, CBC is not a mixture or an alloy of conventional elastomer materials, but is a material in its own right.

Its chemical structure imparts advantageous properties thereto, such as: transparency, low moisture absorption, high purity, high thermal resistance, resistance to ultraviolet (UV), and resistance to acids and to bases.

As a result of its method of manufacture, it is possible to obtain grades going from very stiff to very flexible, similar to thermoplastic elastomers (TPEs).

Using CBC as a sealing element for sealing a metering valve presents numerous advantages, in particular compared to more conventional elastomer materials such as nitrile rubber, EPDM, or polychloroprene rubber:

1) As a result of CBC not containing any double bonds, it is much more neutral than other elastomers; this leads to less interaction with active ingredients.

2) Such saturation also gives it good resistance to aging; this is important in particular for storage, so that the lifetime of the valves is as long as possible.

3) Its high purity gives it a level of extractables that is very low, and once again limits any risk of degrading the active ingredient.

4) Its good chemical resistance ensures good behavior in propellants (with or without alcohol), in particular propellants of the HFA type, and limits the degradation problems that are encountered with such aggressive substances.

5) Its low moisture absorption gives it very good barrier properties against water vapor, and improves the sealing of the valve.

It thus turns out that the use of CBC to make sealing elements makes it possible to improve the operation of metering valves, to reduce interactions with the active substance and/or the propellant gas, and makes the manufacture and the assembly of valves and of inhalers in which the valves are used less difficult or less complicated, and thus less costly.

Although the present invention is described above with reference to an advantageous embodiment thereof, it is naturally not limited thereto, and any useful modifications could be applied thereto without going beyond the ambit of the present invention, as defined by the accompanying claims.

The invention claimed is:

1. A fluid dispenser device comprising: a body (100) that is provided with a dispenser orifice (110); a reservoir (1) containing fluid and a propellant gas; and a metering valve (20) that is assembled on said reservoir (1); said reservoir (1) being movable in said body (100) so as to actuate the metering valve (20) and dispense a dose of fluid through said dispenser orifice (110), said metering valve (20) including a valve member (30) that slides in said metering valve (20) during actuation; said device further comprising at least one sealing element (40, 41, 42) so as to form a leaktight seal, wherein at least one sealing element (40, 41, 42) of said device comprises Cyclic Block Copolymer (CBC).

2. A device according to claim 1, wherein said metering valve (20) is assembled on said reservoir (1) with a neck gasket (40) interposed therebetween.

3. A device according to claim 2, wherein said neck gasket (40) and/or said upper internal gasket (41) and/or said lower internal gasket (42) comprise(s) CBC.

4. A device according to claim 1, wherein said metering valve (20) includes at least one internal gasket (41, 42) that co-operates in leaktight manner with said valve member (30).

5. A device according to claim 4, wherein said metering valve (20) includes an upper internal gasket (41) and a lower internal gasket (42), defining between them a metering chamber (60) of said metering valve (20).

6. A device according to claim 1, wherein said at least one sealing element (40, 41, 42) is constituted by CBC.

7. A device according to claim 1, wherein said fluid is a pharmaceutical fluid containing at least one active substance.

8. A device according to claim 1, wherein said propellant gas comprises HFA gases, in particular of the HFA 134a and/or HFA 227 and/or HFA 152a type.

9. A device according to claim 1, wherein a ring (10) is associated with the metering valve (20), at least one sealing element (40, 41, 42) made of CBC being over-molded on a portion of said metering valve (20) and/or of said ring (10).

* * * * *